(12) United States Patent
Redmond (10) Patent No.: US 8,808,212 B1
(45) Date of Patent: Aug. 19, 2014

(54) ELASTIC SHOULDER SUPPORT DEVICE FOR TRAINING MIND AND MUSCLES FOR PROPER POSTURE

(76) Inventor: Virginia Obana Redmond, Houston, TX (US)

( * ) Notice: Subject to any disclaimer, the term of this patent is extended or adjusted under 35 U.S.C. 154(b) by 435 days.

(21) Appl. No.: 12/930,883

(22) Filed: Jan. 19, 2011

Related U.S. Application Data (60) Provisional application No. 61/336,245, filed on Jan. 19, 2010.

(51) Int. Cl.
| | | |
|---|---|---|
| *A61F 5/37* | (2006.01) | |
| *A61F 13/00* | (2006.01) | |
| *A61B 19/00* | (2006.01) | |
| *A45C 13/30* | (2006.01) | |
| *A45F 3/00* | (2006.01) | |
| *A45F 3/04* | (2006.01) | |
| *A41C 3/00* | (2006.01) | |
| *A41C 3/02* | (2006.01) | |
| *A41C 1/06* | (2006.01) | |
| *A61F 5/00* | (2006.01) | |

(52) U.S. Cl.
USPC ............. 602/19; 128/846; 128/869; 128/870; 128/873; 128/874; 128/876; 224/602; 224/603; 224/604; 224/605; 224/647; 450/1; 450/17; 450/18; 450/23; 450/25; 602/5

(58) Field of Classification Search
USPC ......... 128/846, 869, 870, 873, 874, 875, 876; 224/602–605, 647; 602/19; 450/1, 17, 450/18, 23, 25
See application file for complete search history.

(56) References Cited

U.S. PATENT DOCUMENTS

| | | | |
|---|---|---|---|
| 84,787 A | 12/1868 | Adamson | |
| 370,055 A * | 9/1887 | Haley | 2/45 |
| 665,688 A * | 1/1901 | Hollem | 2/45 |
| 2,233,397 A | 3/1941 | Bloom | 119/857 |
| 3,141,456 A * | 7/1964 | Meek | 602/19 |
| 3,382,868 A * | 5/1968 | Stiefel | 602/19 |
| 3,548,818 A * | 12/1970 | Kaplan | 602/19 |
| 3,856,004 A * | 12/1974 | Cox | 602/19 |
| 3,897,776 A | 8/1975 | Gaylord, Jr. | |
| 4,346,827 A * | 8/1982 | Bianchi et al. | 224/624 |
| 4,570,619 A * | 2/1986 | Gamm | 602/19 |
| 4,785,803 A | 11/1988 | Benckhuijsen | |
| 4,903,874 A * | 2/1990 | Shoemaker | 224/624 |
| 5,120,288 A * | 6/1992 | Sinaki | 482/105 |
| 5,133,340 A * | 7/1992 | Koopmann | 602/19 |
| 6,315,747 B1 * | 11/2001 | Toole | 602/19 |
| 6,387,067 B1 | 5/2002 | Hebert | |
| 6,543,661 B1 * | 4/2003 | Lazur | 224/604 |
| 6,544,205 B1 * | 4/2003 | Herzberg et al. | 602/19 |
| 7,578,798 B2 | 8/2009 | Rhee | |

* cited by examiner

*Primary Examiner* — Patricia Bianco
*Assistant Examiner* — Brandon L Jackson
(74) *Attorney, Agent, or Firm* — Kenneth A. Roddy

(57) ABSTRACT

A shoulder support device includes a flexible elastic continuous ring band and a slide adjustably movable on the band that divides the band into a pair of loops defining arm receiving apertures that are cupped over the curved deltoid region of each shoulder of a wearer to pull the shoulders back and downward under tension to achieve a correct posture position. The slide is moveable to adjust tension distributed to the wearer's shoulders. When the slide is positioned midway between the shoulder blades at the back of the wearer, it provides equal distributed tension on both shoulders. Moving the slide more to the left or more to the right allows the wearer to selectively adjust which shoulder receives more tension.

7 Claims, 8 Drawing Sheets

ELASTIC SHOULDER SUPPORT DEVICE FOR TRAINING MIND AND MUSCLES FOR PROPER POSTURE

CROSS REFERENCE TO RELATED APPLICATION

This application claims priority of U.S. Provisional Application Ser. No. 61/336,245, filed Jan. 19, 2010.

BACKGROUND OF THE INVENTION

1. Field of the Invention

This invention relates generally to posture support devices that brace and support the back and shoulders and, more particularly, to a shoulder support device that includes a flexible elastic continuous ring band and a slide adjustably movable on the band that gathers the band together and divides it into a pair of laterally opposed arm receiving loops which are cupped over the deltoid region of each shoulder of a wearer to pull them back and downward under tension to achieve correct posture.

2. Background Art

In our technology-driven society, people spend many hours slouching and hunching in front of a computer or television monitor, and behind a steering wheel commuting to and from work. During these times, we forget to pay attention to our posture and form. Slouching is a bad habit that occurs unconsciously and can usually be corrected by becoming aware of when you are slouching and straightening the upper back. Prolonged slouching or hunching is linked to health issues such as upper back and neck pain, headaches and compromises breathing. At the end of the day, shoulders and muscles feel the tension that is brought on by incorrect posture and shoulder position and form.

As we become a more health-conscious society we look to meditation, yoga, walking or some type of exercise regiment to keep us fit and limber. To be successful in any of these programs, proper upper body posture and breathing is key. Slouching takes its toll on your body; it can tighten and shorten your chest muscles, restricting your range of motion and causing the wearer to take shallow breaths instead of deep, cleansing ones. Proper posture and breathing can become second nature, but it takes practice, discipline and constant reminding of one's mind and muscles.

Most commercially available shoulder support devices are designed for users who have an existing injury or posture problem, and tend to be very uncomfortable, tight, constraining, cumbersome, expensive and unattractive Some shoulder support devices function as a brace for repairing or immobilizing an existing muscle or clavicle injury, rather than correcting the wearer's shoulder posture and form, and tend to hinder natural upper body movement, forcing the wearer to be in a straight upper position. Some shoulder support devices extend around the shoulders and underneath the armpit and some even extend around the diaphragm. These types of devices typically require the bands to be pulled tighter in order to pull the shoulders back, making wearing of these devices tight and uncomfortable. The elastic bands used in many posture supports cause irritation beneath the arms due to the tightness of the band.

Many shoulder support devices fall into the category of a medical or orthopedic apparatus or an undergarment and are typically unattractive and unappealing to one who needs to wear the device in public. Some devices give the impression that the wearer has a physical problem. Some devices alert a person when they start to slouch by a sound or vibration. These types of devices are usually attached to the wearer's undergarment. The problem with these types of devices is that they merely alert the wearer that they are no longer in the correct posture form, and are incapable of teaching what the proper form should be.

When one slouches, the shoulders move forward and upward. Most commercially available shoulder support devices tend to only focus on stretching the shoulder muscles back and ignore the fact that the shoulders and neck muscles also need to be stretched downward as well. Although slouching is a forward and upward motion of the shoulders, not everyone's shoulders slouch evenly. Most shoulder support devices are designed around the assumption that both of the wearer's shoulders need to be pulled back with the same amount of tension, and are incapable of allowing selective tension adjustment for each shoulder individually.

Thus, a need exists for a comfortable, fashionable shoulder support device that facilitates training the mind and muscles of a wearer to achieve correct shoulder posture and form before it becomes a health issue and that cups the shoulders and gently pulls them back and downward under tension while allowing natural movement and allows selective tension adjustment for each shoulder individually.

SUMMARY OF THE INVENTION

As used herein, the anatomical term "deltoid region" of the shoulder means the lateral aspect of the shoulder demarcated by the outlines of the deltoid muscle. The term "lateral aspect" refers to a position that is further from (lateral) the midline of the body, as opposed to "medial" which refers to a position that is closer to (medial) to the midline of the body. The deltoid muscle is the muscle forming the outwardly rounded contour of the shoulder. Anatomically, the deltoid muscle appears to "cap" the shoulder joint. It has a generally upside-down teardrop shape, and consists of three portions—the front section (anterior deltoid), the side section (lateral deltoid), and the back section (posterior deltoid).

The present invention is distinguished over the prior art in general, and these patents in particular by a shoulder support device that includes a band member made of a flexible elastic material, in the form of a continuous ring, and a slide member which has a divider in the center that gathers the band together and divides it into a pair of laterally opposed arm receiving loops that define arm receiving openings or apertures. The loops extend over and gently cup the curved deltoid region of each shoulder while pulling them slightly back and downward under tension. The slide is moveable on the band to adjust tension distributed to the wearer's shoulders. When the slide is placed directly in the center midway between the shoulder blades, it assures equal distributed tension on both sides of the band giving a gentle pull on the wearer's shoulders. Moving the slide more to the left or more to the right allows the wearer to selectively adjust which shoulder receives more tension.

The shoulder support device cups the curved deltoid region of the wearer's shoulders and gently pulls the shoulders back and downward under tension to help the wearer be mindful of their muscles and proper shoulder posture form. Proper shoulder becomes effortless when using the device. The present shoulder support device cups the wearer's shoulders without causing irritation or cutting into the skin. The elastic material conforms to the curved shape of the deltoid region of the wearer's shoulders and is comfortable while allowing natural movement. The device may be worn over clothing, but can be worn underneath clothing as well.

DESCRIPTION OF THE PREFERRED EMBODIMENT

Referring to the drawings by numerals of reference, there is shown in FIGS. 1A, 1B, 1C, 1D, and, a shoulder support device 10 in accordance with the present invention. The shoulder support device 10 includes an elastic continuous ring band member 11 and a slide member 14 which has a divider 16 in the center that gathers the band together and divides it into a pair of laterally opposed arm receiving loops 12 that define arm receiving openings or apertures 13. As discussed hereinafter, the shoulder support device 10 gently cups the curved deltoid region of each shoulder of the wearer while pulling the shoulders slightly back and downward under tension. The slide 14 is moveable on the band to selectively adjust tension distributed to the wearer's shoulders.

Figure 1A:
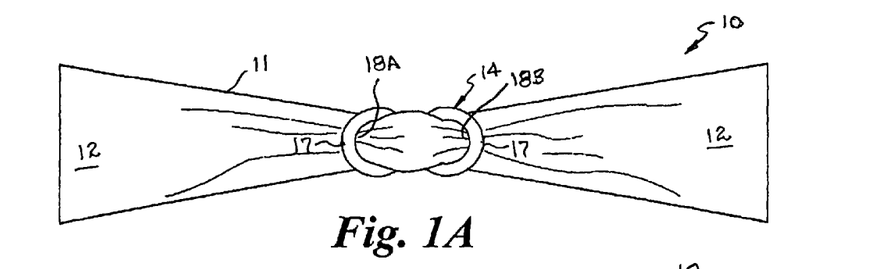
FIGS. 1A and 1B are a front elevation and a rear elevation view, respectively, of the shoulder support device in accordance with the present invention, shown with the band and slide members in an assembled condition.
Figure 1B:
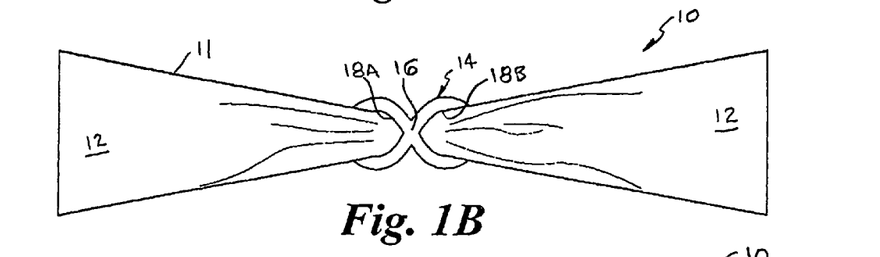
Figure 1C:
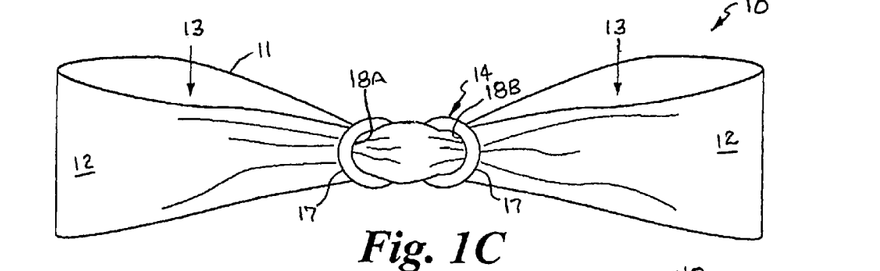
FIGS. 1C and 1D are perspective views of the assembled shoulder support device shown from the front and side, respectively, more clearly showing the loops defining arm receiving openings.
Figure 1D:
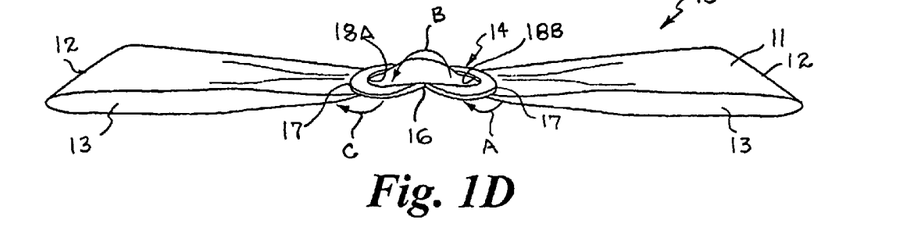
Figure 2A:
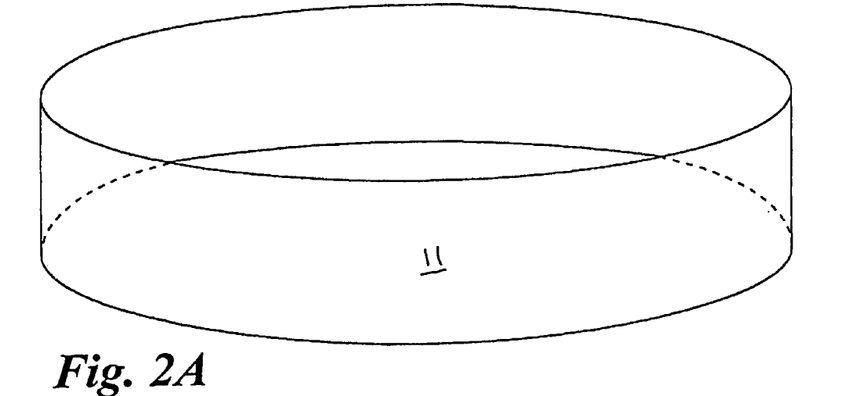
FIGS. 2A and 2B are perspective views of the continuous band member.
Figure 2B:
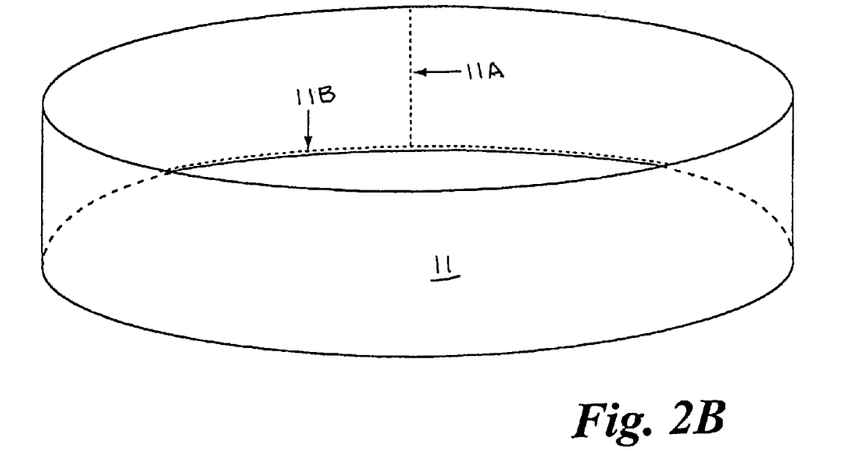

Referring additionally to FIGS. 2A and 2B, the continuous ring band 11 is made of a flexible elastic material, and may be integrally formed or molded, or may be made of a length of flexible elastic material, the ends of which are secured together by conventional means. For example, but not limited thereto, the continuous ring band 11 may be formed of a length of flexible elastic material, the ends of which are secured together by sewing 11A, to create the continuous ring, folded such that the top edge meets the bottom edge and sewn together as indicated at 11B, then turned inside out to create the finished band. The elastic continuous ring band 11 has a transverse width sufficient to be extended over and cup the curved deltoid region of each shoulder of a wearer, as described hereinafter. Various sizes of bands may be provided for different wearers (children, women, men sizes). It should be understood that the band can be created by various different processes (not necessarily sewn) so long as the end result is a continuous ring.

Figure 3A:
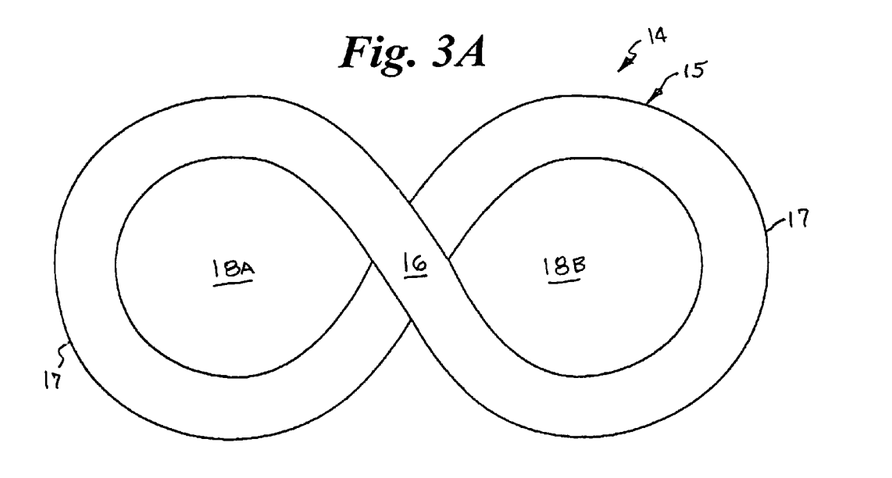
FIGS. 3A and 3B are a top plan view and a perspective view of the slide member.
Figure 3B:
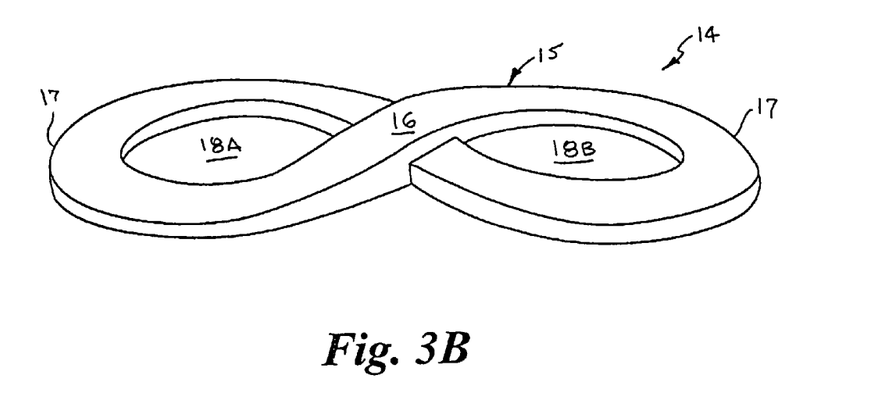
Figure 4:
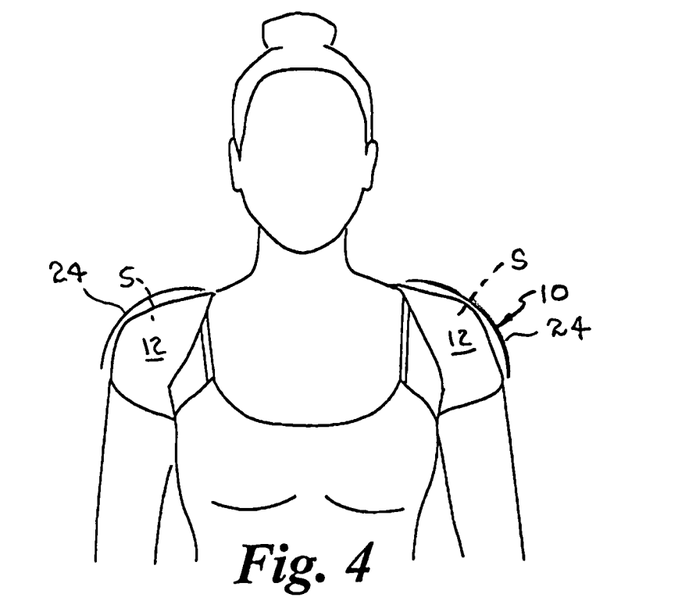
FIGS. 4 and 5 are pictorial and rear views showing the shoulder support device properly positioned on a wearer.
Figure 5:
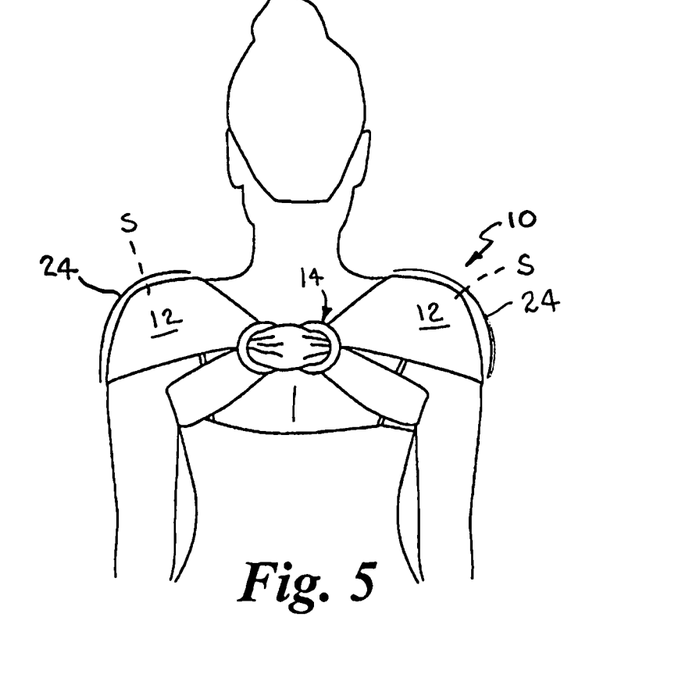
Figure 6:
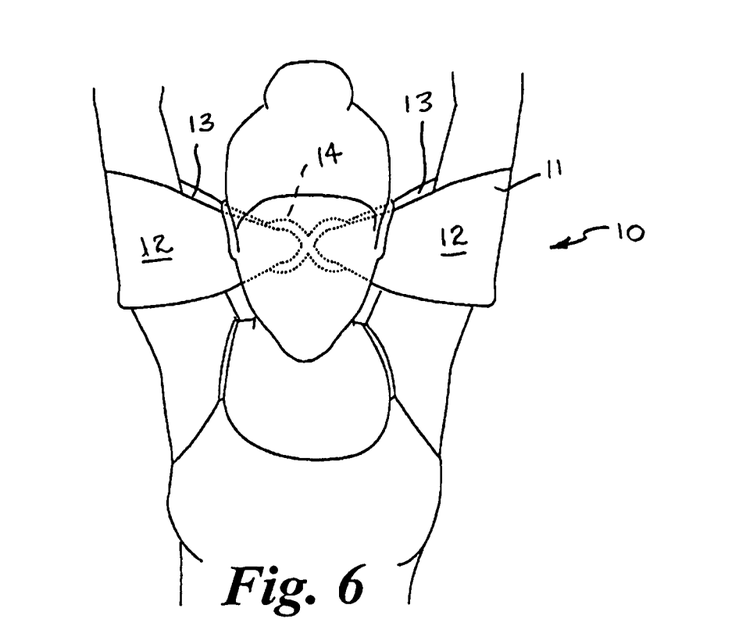
FIGS. 6, 7, 8A, 8B, and 9-11 are pictorial views illustrating the steps of how the shoulder support device is placed on the wearer and adjustably positioned for proper use.

Referring additionally to FIGS. 3A and 3B, the slide 14 is formed or molded of a rigid material having a peripheral frame 15 with a central divider 16 and outer sides 17 defining laterally adjacent first and second openings 18A, 18B, equal in size and shape. In the illustrated example of a preferred embodiment, but not limited thereto, the slide 14 has a generally "figure-8" configuration. It should be understood that the slide 14 may be configured differently from the illustrated example. The rigid slide material is of sufficient thickness and strength to withstand the pulling and stretching of the elastic band.

In the illustrated example of the slide having a generally "figure-8" configuration, but not limited thereto, the slide may be about 57 mm wide×124 mm in length×3 mm in thickness, or may be sized down or up, so as to be proportional to those measurements. In this example, the two openings 18A, 18B of the slide 14 each may have an opening measurement of about 40 mm×35 mm wide or proportional to this size. If the center divider 16 of the slide 14 overlaps to create the "figure-8" configuration, the center thickness may be double the thickness of the outer sides 17 of the slide.

Referring again to FIG. 1D, as indicated by arrows A, B, and C, the device 10 is assembled by placing the band 11 in a flat condition, feeding one end of the flattened band through the first opening 18A or 18B of the slide, over the top of the center divider 16, then back down through the second opening of the slide, and pulled through the slide until the slide is generally centered on the band. When viewed from the outer facing side of the device (FIGS. 1A, 1C), only the outer sides 17 of the slide 14 will be seen; the center divider 16 of the slide is hidden underneath the portion of the band that extends over the center divider 16 of the slide. The slide 14 gathers the band 11 together and creates the two laterally opposed loops 12 defining the arm receiving openings or apertures 13 in the band.

OPERATION

Referring now to FIGS. 4-7, 8A, 8B, and 9-11, the steps of how the shoulder support device 10 is placed on the wearer and adjustably positioned for proper use. When preparing to wear the shoulder support device 10, it should be positioned so that the arm receiving openings or apertures 14 of the loops 12 are disposed vertically at the top and bottom rather than horizontally. This will allow the loops 12 to be cupped over the curved deltoid region 24 of the shoulders S and hold the shoulders slightly back and downward (FIGS. 4 and 5) under tension once it is properly positioned on the wearer.

Figure 7:
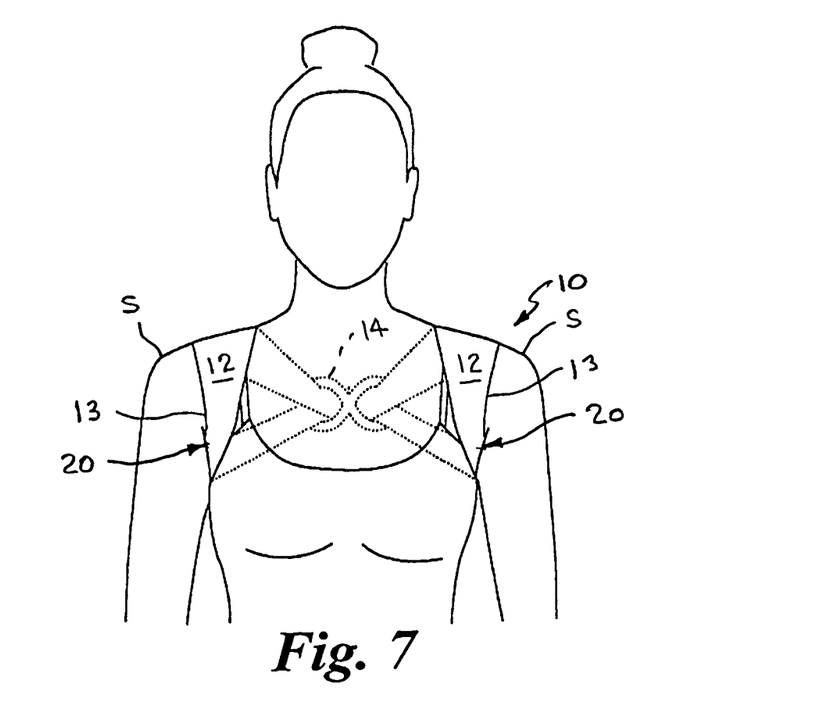
Figure 8A:
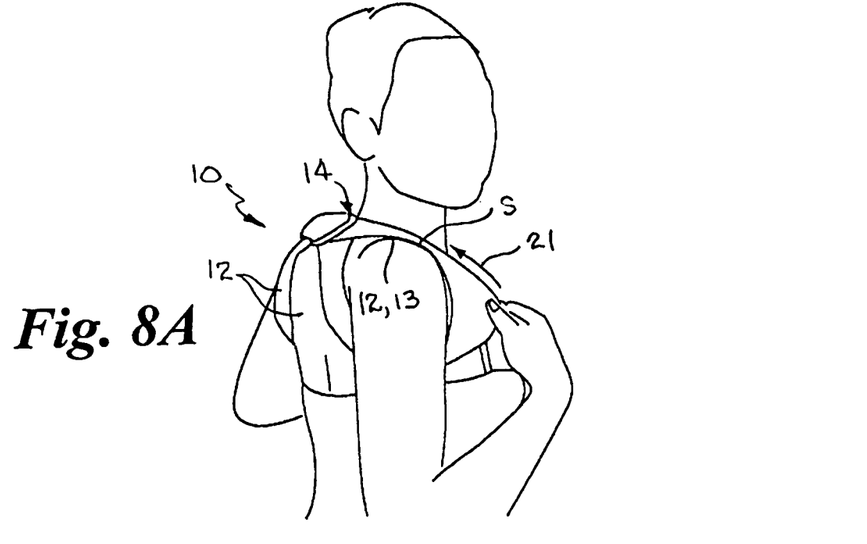
Figure 8B:
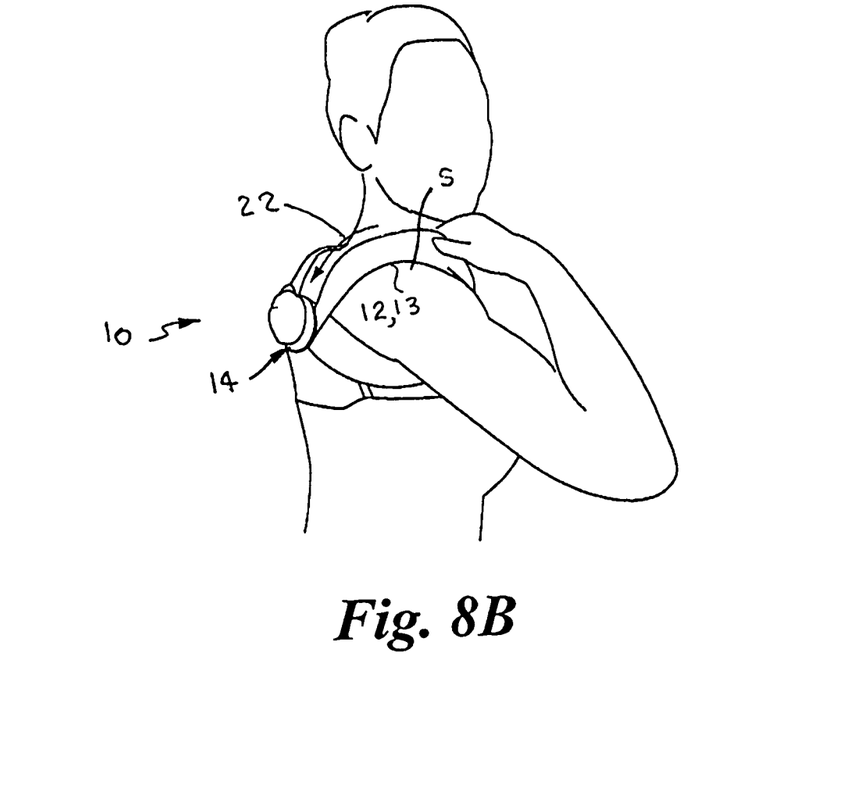
Figure 9:
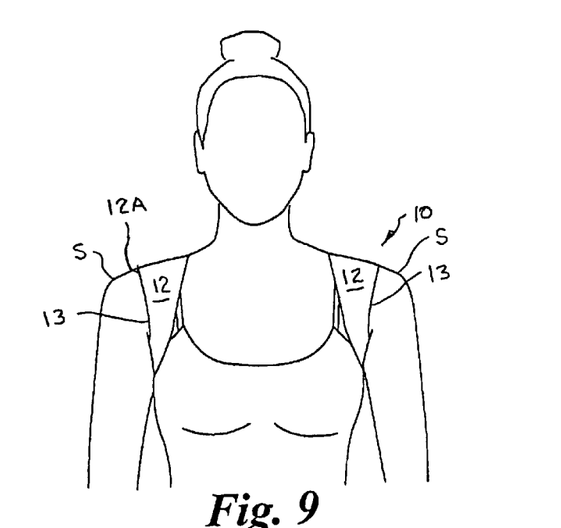
Figure 10:
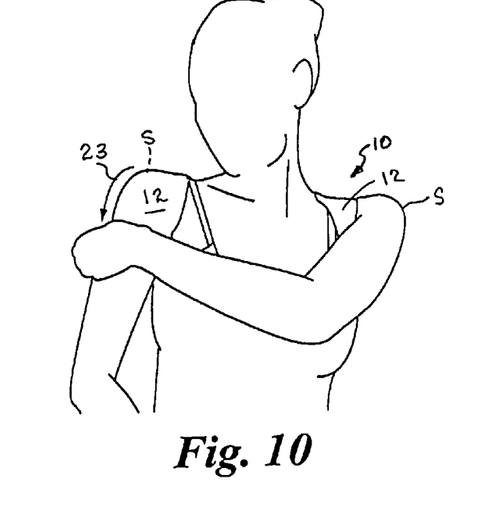
Figure 11:
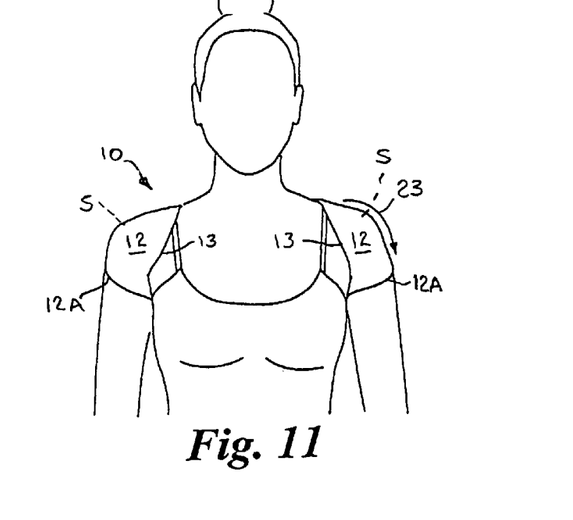

The wearer raises both arms straight up (FIG. 6) and places one arm through the opening or aperture 13 of the first loop 12 of the band 11 and the other arm through the opening or aperture of the second loop and allows the band slide down to their shoulders, making sure that the band is behind their head. After the band has slid down to the armpit area, as indicated at 20, the wearer then brings their arms back down to their side as shown in FIG. 7 with the band 11 disposed flat behind their shoulder blades and the slide 14 generally centered flat against their back and between the shoulder blades. The center divider 16 of the slide 14 that is not covered by the band should be face-to-face with the wearer's back (FIG. 7). The wearer may then adjust the left and right loops 12 by pulling them slightly upward and over their shoulders S as indicated by arrow 21 (FIG. 8A) until the slide 14 shifts lower down between the center of their shoulder blades and away from the nape of the neck as indicated by arrow 22 (FIG. 8B). Once the slide 14 is in position, the wearer grasps the outer side edge 12A (FIG. 9) of the outer portion of a first loop 12 and, and as indicated by arrow 23, pulls it over the curved deltoid region 24 of one shoulder S so that it holds and cups the deltoid region of the shoulder (FIG. 10) and then repeats the process for the other shoulder (FIG. 11). The tension of the band 11 should allow for even and natural movement of the shoulders S but will maintain a gentle back and downward even tension pull on the shoulders to prevent hunched or slouching forward of the shoulders. The tension should not be so tight that proper form is hindered. During some movement of the arms, readjusting the band to the proper position may be necessary.

Referring again to FIGS. 4 and 5, shoulder support device 10 gently cups the deltoid region 24 of each shoulder S of the wearer (FIG. 5) while pulling the shoulders slightly back and downward. The loop 12 of the band 11 conforms to the curved shape of the deltoid region of the wearer's shoulders due to the elastic material. When the slide 14 is placed directly in the center midway between the shoulder blades, it assures equal distributed tension on both sides of the band giving a gentle pull on the wearer's shoulders. Moving the slide 14 more to the left or more to the right of center allows the wearer to selectively adjust which shoulder receives more tension. In other words, when the slide 14 is in a generally centered position each of the loops 12 are of generally equal size to apply generally equal tension to both shoulders S; and when the slide is moved to one side or the other from the centered position, the loops are of unequal size to apply more tension to one shoulder than to the other. Thus, the wearer can easily selectively adjust which shoulder receives more tension.

Figure 12:
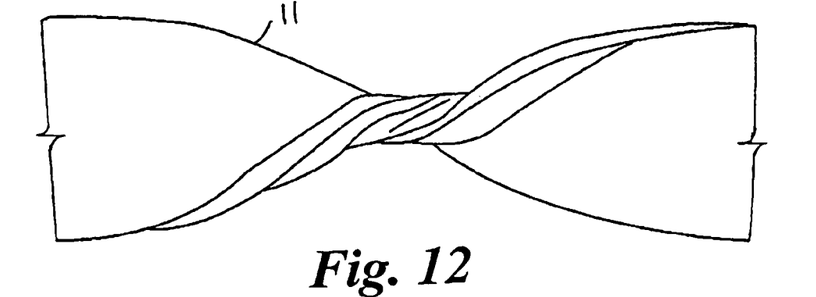
FIGS. 12 and 13 are front elevation views illustrating an example of how the tension of the band may be adjusted.
Figure 13:
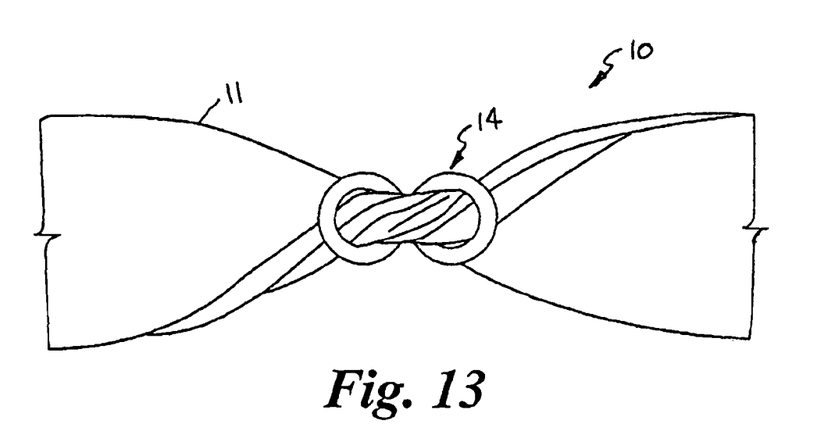

As shown somewhat schematically in FIGS. 12 and 13, the wearer can also adjust the length and, thus, the tension of the band 11 by twisting the band once, twice or three times (FIG. 12), depending on how tight the wearer wants the tension to be. To adjust the tension, the wearer places one arm through the opening or aperture of a first loop, and with the slide on the band (FIG. 13), the band is twisted as many times needed; typically up to 3 times. Once the band has been twisted, the other arm is placed through the other opening or aperture of the second loop. The wearer then lifts their arms and lets the band slide down to their shoulders, making sure that the band is behind their head, as described previously. If the tension of the band does not allow the band to freely slide down by itself, then it may be manually pulled down to the armpit area. After the band is down to the armpit area, the wearer can then bring their arms down to their side. If the band has been twisted, it may be necessary to adjust the slide 14 such that that the center of the slide that is not covered by the fabric band is flat against the wearer's back and in between the shoulder blades. The wearer may then adjust the left and right loops by pulling them slightly upward and over their shoulders until the slide is disposed between the center of their shoulder blades and away from the nape of the neck, as described above, and then in turn, grasp the outer portion the loops and pull them over the curved deltoid region of the shoulder, as also described above.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A shoulder support device for facilitating correct posture of shoulders of a wearer, the shoulder support device comprising:

a continuous ring band formed of flexible elastic material having a transverse width sufficient to extend over, conform to, and cup a curved deltoid region of the lateral aspect of each shoulder of the wearer;

a slide member slidably and adjustably disposed on said continuous ring band, said slide having a peripheral frame with a central divider defining laterally adjacent first and second openings each having a width smaller than said transverse width of said continuous ring band, and said continuous ring band in a flattened condition extending through said first opening, over said central divider, and through said second opening so as to narrow said transverse width of said continuous ring band at a mid portion thereof and divide said band into a pair of laterally opposed loops defining arm receiving apertures, each diverging outwardly from a narrower width portion adjacent to said slide member to a wider outer side portion; wherein said wider outer side portion of each of said loops is received on and is stretched over the curved deltoid region of the lateral aspect of each shoulder of the wearer to cup and conform to the curvature thereof, respectively, and said slide is disposed at the back side of the wearer adjacent to the wearer's shoulder blades to pull the wearer's shoulders back and downward under tension to achieve a proper posture position.

2. The shoulder support device according to claim 1, wherein said slide peripheral frame has a generally figure eight configuration.

3. The shoulder support device according to claim 2, wherein said laterally opposed loops are rotatable relative to one another to twist said mid portion of said band extending through said slide and shorten the overall length of said band to increase tension applied by said band when said wider outer side portion of each of said loops is stretched over the curved deltoid region of the lateral aspect of each shoulder of the wearer.

4. The shoulder support device according to claim 1, wherein said slide is slidably and adjustably moveable on said band between a generally centered position such that each of said loops are of generally equal length to apply generally equal tension to both shoulders; and said slide is selectively movable to one side or the other from said centered position such that said loops are of unequal length to apply more tension to one shoulder than the other to selectively adjust which shoulder receives more tension.

5. A method of supporting shoulders to facilitate correct posture of shoulders of a wearer, the method comprising the steps of:

providing a shoulder support device having a continuous ring band formed of flexible elastic material having a transverse width sufficient to extend over, conform to, and cup a curved deltoid region of the lateral aspect of each shoulder of the wearer and a slide member slidably and adjustably disposed thereon, said slide having a peripheral frame with a central divider defining laterally adjacent first and second openings each having a width smaller than said transverse width of said continuous ring band, and said continuous ring band in a flattened condition extending through said first opening, over said central divider, and through said second opening so as to narrow said transverse width of said continuous ring band at a mid portion thereof and divide said band into a pair of laterally opposed loops defining arm receiving apertures, each diverging outwardly from a narrower width portion adjacent to said slide member to a wider outer side portion of sufficient width and elasticity to be received on, cupped over, and conform to the curved deltoid region of the lateral aspect of each shoulder of the wearer, respectively;

placing the loops over the shoulders with arms of the wearer extending through the apertures such that the device is behind the wearers head and the loops encircle the shoulders with the slide generally centered flat against a back side of the wearer;

pulling the wider outer side portion of each loop over the curved deltoid region of the lateral aspect of the shoulders to extend over, conform to, and cup the curved deltoid region of the shoulders; whereby the wearer's shoulders are pulled back and downward under tension to achieve a proper posture position.

6. The method according to claim 5, comprising the further step of:

moving said slide to a generally centered position such that each of said loops are of generally equal length to apply generally equal tension to both shoulders.

7. The method according to claim 5, comprising the further step of:

selectively moving said slide on said band to one side or the other from said centered position such that said loops are of unequal length to apply more tension to one shoulder than the other to adjust which shoulder receives more tension.

\* \* \* \* \*